United States Patent [19]

Hodosh

[11] 4,400,373
[45] Aug. 23, 1983

[54] METHOD FOR TREATING GINGIVAL AND PERIODONTAL TISSUES

[76] Inventor: Milton Hodosh, 72 Overhill Rd., Providence, R.I. 02906

[21] Appl. No.: 331,456

[22] Filed: Dec. 15, 1981

[51] Int. Cl.³ .................... A61K 7/16; A61K 33/00
[52] U.S. Cl. ................................. 424/49; 424/127
[58] Field of Search ................................. 424/49, 127

[56] References Cited

U.S. PATENT DOCUMENTS 3,863,006 1/1975 Hodosh ................................. 424/49

OTHER PUBLICATIONS

Chem. Abst. 81:86224(h) (1974)—Hodosh.
Chem. Abst. 84:79709(d) (1976)—Hodosh.

Primary Examiner—Douglas W. Robinson
Attorney, Agent, or Firm—Salter & Michaelson

[57] ABSTRACT

A compound and method of treating gingival and periodontal tissues, the essential ingredient of said compound comprising potassium nitrate, and the method comprising the application of said compound in aqueous solution or nontoxic paste form to said tissue.

7 Claims, No Drawings

METHOD FOR TREATING GINGIVAL AND PERIODONTAL TISSUES

BACKGROUND AND SUMMARY OF THE INVENTION

The importance of maintaining proper gingival and periodontal health has been well established. The factors normally evaluated in determining the heath of a patient's periodontium are the following:

(1) gingival tone, texture and consistency;
(2) gingival attachment as measured in the sulcus (6 reference points about each tooth) with a calibrated periodontal probe;
(3) gingival enlargement;
(4) gingival bleeding when provoked by instrumentation (amount and length of time of bleeding);
(5) the presence of chronic destructive periodontal disease which, if advanced, will threaten loss of dentition, i.e. severe bone loss, tooth mobility, deep pocket formation, bleeding, etc.;
(6) the presence of pain or discomfort to the patient.

Treatment of the foregoing may comprise regular and periodic massaging of the gingivae, tooth brushing and rinsing of the mouth on a regular basis, deep scaling and curettage procedures performed by dentists, bacterial control and in extreme cases, surgical procedures may become necessary.

In accordance with the present invention, it has been found that the health of gingival and periodontal tissues may be effectively maintained and/or improved by the application to said tissues of an agent, the essential ingredient of which is potassium nitrate. the beneficial effects of potassium nitrate as a treatment for certain specific oral problems have heretofore been well documented, note applicant's U.S. Pat. No. 3,863,006 dated Jan. 28, 1975; applicant's U.S. Pat. No. 4,191,750 dated Mar. 4, 1980; and applicant's co-pending U.S. patent application Ser. No. 126,433, filed Mar. 3, 1980 now U.S. Pat. No. 4,343,608. However, the use of potassiun nitrate as the active ingredient in an agent for treating gingival and periodontal tissues has not heretofore been known and actually forms the basic and salient concept of the present invention.

DESCRIPTION OF THE INVENTION

It has been found that the application of potassium nitrate, either in an aqueous solution or as a part of a nontoxic paste, to the teeth gingival and periodontal tissues is amazingly effective in maintaining or improving the health of said tissues. Specifically, an aqueous solution or paste comprising approximately five percent (5%) by weight potassium nitrate, when used regularly as a mouthwash, has been found to reduce gingival bleeding and at the same time clinically improve the texture and consistency of said tissues. Gingival tissues so treated were found to be less tender and pocket depths were substantially reduced, i.e., gingival enlargements were diminished resulting in improved contours, texture and consistency.

Although an aqueous solution comprising approximately five percent (5%) by weight potassium nitrate has proven to be particularly effective, an aqueous solution comprising potassium nitrate anywhere in the range of one percent (1%) by weight to saturation also has efficacy. For best results the mouthwash must be used on a regular basis, i.e., two or three times a day, with the solution being held in the patient's mouth for one and one-half to two minutes in order to allow the potassium nitrate to adequately engage the gingival and periodontal tissues. It has been found that such a solution, when used on a regular basis, and particularly when employed in combination with periodic deep scaling and curettage procedures performed by the patient's dentist results in substantial pocket reduction. Expressed differently, the application of the potassium nitrate solution on a regular basis serves to enhance the reduction of pocket depth that will normally take place pursuant to conventional deep scaling and curettage procedures. Also, the application of the potassium nitrate solution on a regular basis pursuant to the instant invention results in a marked lessening of bleeding in those patients subject to abnormal gingival bleeding. This reduction in bleeding is particularly noticeable during brushing and during examination of the patient's teeth and gums with instrumentation.

The same results are achieved where the potassium nitrate is mixed with a nontoxic paste or cream which is then gently massaged into the gums two or three times daily. Here again a paste or cream having five percent (5%) potassium nitrate by weight has proven to be particularly effective, although a paste or cream having potassium nitrate anywhere in the range of one percent (1%) to saturation, i.e. approximately twenty-three percent (23%). by weight is also effective in varying degrees.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. The method of reducing gingival bleeding and improving the texture and consistency of gingival and periodontal tissues by applying thereto a composition comprising about 1–23% by weight of potassium nitrate.

2. The method of claim 1 further characterized in that said composition comprises potassium nitrate in an aqueous solution.

3. The method of claim 2 further characterized in that said potassium nitrate comprises between approximately five percent (5%) by weight and saturation of said aqueous solution.

4. The method of claim 1 further characterized in that said composition comprises potassium nitrate mixed with a nontoxic paste.

5. The method of claim 4 further characterized in that said potassium nitrate comprises approximately five percent (5%) by weight of said paste.

6. The method of reducing gingival bleeding and improving the texture and consistency of gingival and periodontal tissues by applying thereto an aqueous solution, the essential ingredient of which is potassium nitrate, said potassium nitrate comprising between one percent (1%) by weight and saturation (approximately 20%) of said aqueous solution.

7. The method of reducing gingival bleeding and improving the texture and consistency of gingival and periodontal tissues by applying thereto a nontoxic paste, the essential ingredient of which is potassium nitrate, said potassium nitrate comprising between one percent (1%) and saturation (approximately 23%) of said paste.

* * * * *